(12) United States Patent
Ma et al.

(10) Patent No.: US 10,351,840 B2
(45) Date of Patent: *Jul. 16, 2019

(54) REVERSE TRANSCRIPTASE MIXTURES WITH IMPROVED STORAGE STABILITY

(71) Applicant: Bio-Rad Laboratories, Inc., Hercules, CA (US)

(72) Inventors: Jason Ma, Hercules, CA (US); Xiao-Song Gong, Richmond, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 95 days.

This patent is subject to a terminal disclaimer.

(21) Appl. No.: 15/253,648

(22) Filed: Aug. 31, 2016

(65) Prior Publication Data

US 2016/0369260 A1 Dec. 22, 2016

Related U.S. Application Data

(63) Continuation of application No. 13/277,763, filed on Oct. 20, 2011, now Pat. No. 9,458,484.

(51) Int. Cl.
| | |
|---|---|
| *C12N 9/96* | (2006.01) |
| *C12P 19/34* | (2006.01) |
| *C12N 9/12* | (2006.01) |
| *C12N 15/10* | (2006.01) |
| *C12Q 1/686* | (2018.01) |

(52) U.S. Cl.
CPC .............. *C12N 9/96* (2013.01); *C12N 9/1276* (2013.01); *C12N 15/1096* (2013.01); *C12P 19/34* (2013.01); *C12Q 1/686* (2013.01); *C12Y 207/07049* (2013.01); *Y02P 20/52* (2015.11)

(58) Field of Classification Search
None
See application file for complete search history.

(56) References Cited

U.S. PATENT DOCUMENTS

| | | |
|---|---|---|
| 5,935,834 A | 8/1999 | Odawara |
| 6,294,365 B1 | 9/2001 | De Rosier et al. |
| 6,767,724 B2 | 7/2004 | Lee et al. |
| 7,112,407 B2 | 9/2006 | Ishiguro et al. |
| 2009/0155777 A1 | 6/2009 | Yang et al. |
| 2010/0221786 A1 | 9/2010 | Jeong et al. |
| 2012/0129238 A1 | 5/2012 | Ma et al. |

FOREIGN PATENT DOCUMENTS

| | | |
|---|---|---|
| WO | 9426934 | 11/1994 |
| WO | 2012054727 | 4/2012 |

OTHER PUBLICATIONS

"Superscript II Reverse Transcriptase", Invitrogen, Life Technologies, May 2010, pp. 1-4.
PCT/US2011/057103, "International Search Report and Written Opinion", dated Mar. 2, 2012, 22.

*Primary Examiner* — Paul J Holland
(74) *Attorney, Agent, or Firm* — Kilpatrick Townsend and Stockton LLP

(57) ABSTRACT

Reverse transcriptase mixtures with improved storage stability are provided.

16 Claims, 5 Drawing Sheets

US 10,351,840 B2

REVERSE TRANSCRIPTASE MIXTURES WITH IMPROVED STORAGE STABILITY

CROSS-REFERENCE TO RELATED PATENT APPLICATIONS

The present patent application is a continuation of U.S. patent application Ser. No. 13/277,763, filed Oct. 20, 2011, which claims benefit of priority to U.S. Provisional Patent Application No. 61/405,961, filed on Oct. 22, 2010, which is incorporated by reference for all purposes.

BACKGROUND OF THE INVENTION

The detection, analysis, transcription, and amplification of nucleic acids are frequently-used procedures in modern molecular biology. The application of such procedures for RNA analysis can involve the investigation of gene expression, diagnosis of infectious agents or genetic diseases, and the generation of cDNA, to name but a few applications. The reverse transcription ("RT") of RNA thus has many uses. In some instances, the RT is followed by polymerase chain reaction amplification which can be used for rapid detection and quantification of RNA. This procedure is often referred to as "RT-PCR".

BRIEF SUMMARY OF THE INVENTION

The present invention provides for reaction mixtures for reverse transcription of RNA in a sample. In some embodiments, the mixture comprises: a reverse transcriptase having an optimal pH above 8; and a buffer, wherein the mixture has a pH of between 6-8, lacks template RNA, and the reverse transcriptase maintains essentially all (e.g., at least 95% of original) reverse transcriptase activity following incubation of the mixture at 50° C. for 30 minutes.

In some embodiments, the reaction mixture comprises sufficient ingredients (i.e., such that upon addition of template RNA, under conditions (e.g., temperature) appropriate for the RT enzyme, reverse transcription occurs), except template RNA, for reverse transcription of RNA.

In some embodiments, the buffer (when measured at a concentration of 0.1 M) has a change of no more than 0.027 pH units per degree C. when between 20° and 37° C. In some embodiments, the buffer is selected from the group consisting of HEPES, ACES, PIPES, MOPSO, BES, MOPS, TES, TAPSO, POPSO, BICINE, TAPS, and AMPSO.

In some embodiments, the reaction mixture further comprises one or more polyols having a total concentration of at least 15%. In some embodiments, the polyol is an alcohol having four or more, or five or more, carbons. In some embodiments, the polyol (e.g., alcohol) is selected from the group consisting of sorbitol and xylitol. In some embodiments, the total concentration of polyols, or total concentration of at least four carbon alcohols, is at least 25%.

In some embodiments, the total concentration of polyols, or total concentration of at least four carbon alcohols, is at least 35%.

In some embodiments, the mixture has a pH less than 8. In some embodiments, the mixture has a pH between 7-8. In some embodiments, the mixture has a pH between 7.4-7.8.

In some embodiments, the reverse transcriptase is selected from the group consisting of murine leukemia virus (MLV) reverse transcriptase, Avian Myeloblastosis Virus (AMV) reverse transcriptase, Respiratory Syncytial Virus (RSV) reverse transcriptase, Equine Infectious Anemia Virus (EIAV) reverse transcriptase, Rous-associated Virus-2 (RAV2) reverse transcriptase, SUPERSCRIPT II reverse transcriptase, SUPERSCRIPT I reverse transcriptase, THERMOSCRIPT reverse transcriptase and MMLV RNase H-reverse transcriptase.

In some embodiments, the mixture further comprises potassium chloride, magnesium, deoxytriphosphate nucleotides, one or more detergents, an oligo dT, an oligonucleotide other than an oligo dT, an RNase inhibitor, or a combination thereof.

In some embodiments, the reaction mixture is sterile.

The present invention also provides for reaction mixtures comprising: a reverse transcriptase; and a buffer (when measured at a concentration of 0.1 M) that has a change of no more than 0.027 pH units per degree C. when between 20° and 37° C. and when stored within a pH range of 6-8; wherein the mixture lacks template RNA and the reverse transcriptase maintains essentially all reverse transcriptase activity following incubation at 50° C. for 30 minutes.

In some embodiments, the reverse transcriptase has an optimal pH above 8.

In some embodiments, the reaction mixture comprises sufficient ingredients, except template RNA, for reverse transcription of RNA.

In some embodiments, the buffer is selected from the group consisting of HEPES, ACES, PIPES, MOPSO, BES, MOPS, TES, TAPSO, POPSO, BICINE, TAPS, and AMPSO.

In some embodiments, the reaction mixture has a pH from 6-8. In some embodiments, the mixture has a pH less than 8. In some embodiments, the mixture has a pH between 7-8. In some embodiments, the mixture has a pH between 7.4-7.8.

In some embodiments, the reverse transcriptase is selected from the group consisting of murine leukemia virus (MLV) reverse transcriptase Avian Myeloblastosis Virus (AMV) reverse transcriptase, Respiratory Syncytial Virus (RSV) reverse transcriptase, Equine Infectious Anemia Virus (EIAV) reverse transcriptase, Rous-associated Virus-2 (RAV2) reverse transcriptase, SUPERSCRIPT II reverse transcriptase, SUPERSCRIPT I reverse transcriptase, THERMOSCRIPT reverse transcriptase and MMLV RNase H-reverse transcriptase.

In some embodiments, the mixture further comprises potassium chloride, magnesium, deoxytriphosphate nucleotides, one or more detergents, an oligo dT, an oligonucleotide other than an oligo dT, an RNase inhibitor, a polyol (e.g., wherein the polyol is a four or more, or five or more, carbon alcohol), or a combination thereof.

In some embodiments, the reaction mixture is sterile.

The present invention also provides a mixture comprising: a reverse transcriptase; a buffer; and one or more polyols having a total concentration of at least 15%, wherein the mixture lacks template RNA and the reverse transcriptase maintains essentially all reverse transcriptase activity following incubation at 50° C. for 30 minutes. In some embodiments, the polyol(s) is a four or more, or five or more, carbon alcohol. In some embodiments, the polyol is selected from sorbitol and xylitol.

In some embodiments, sufficient ingredients, except template RNA, for reverse transcription of RNA.

In some embodiments, the buffer (when measured at a concentration of 0.1 M) has a change of no more than 0.027 pH units per degree C. when in liquid form between 20° and 37° C. In some embodiments, the buffer is selected from the group consisting of HEPES, ACES, PIPES, MOPSO, BES, MOPS, TES, TAPSO, POPSO, BICINE, TAPS, and AMPSO.

In some embodiments, the total concentration of the polyols (e.g., four or more, or five or more, carbon alcohol) is at least 25%. In some embodiments, the total concentration of the polyols (e.g., four or more or five or more carbon alcohol) is at least 35%.

In some embodiments, the reverse transcriptase has an optimal pH above 8.

In some embodiments, the mixture has a pH between 6-8. In some embodiments, the mixture has a pH between 7-8. In some embodiments, the mixture has a pH less than 8. In some embodiments, the mixture has a pH between 7.4-7.8.

In some embodiments, the total concentration of polyols (e.g., four or more, or five or more, carbon alcohols) is at least 25%. In some embodiments, the total concentration of polyols (e.g., four or more, or five or more, carbon alcohols) is at least 35%. In some embodiments, the reverse transcriptase is selected from the group consisting of murine leukemia virus (MLV) reverse transcriptase Avian Myeloblastosis Virus (AMV) reverse transcriptase, Respiratory Syncytial Virus (RSV) reverse transcriptase, Equine Infectious Anemia Virus (EIAV) reverse transcriptase, Rous-associated Virus-2 (RAV2) reverse transcriptase, SUPERSCRIPT II reverse transcriptase, SUPERSCRIPT I reverse transcriptase, THERMOSCRIPT reverse transcriptase and MMLV RNase H-reverse transcriptase.

In some embodiments, the mixture further comprises potassium chloride, magnesium, deoxytriphosphate nucleotides, one or more detergents, an oligo dT, an oligonucleotide other than an oligo dT, an RNase inhibitor, or a combination thereof.

In some embodiments, the reaction mixture is sterile.

The present invention also provides for methods of reverse transcribing RNA. In some embodiments, the method comprises, contacting a reaction mixture of the invention as described above or elsewhere herein with a sample comprising RNA under conditions to allow the reverse transcriptase to reverse transcribe the RNA, thereby producing a first-strand cDNA.

In some embodiments, the conditions comprise a reverse transcription temperature higher than 42° C.

In some embodiments, the method further comprises forming a second-strand cDNA.

The present invention also provides for storing an RNA-free ready-to-use reverse transcriptase mixture, the method comprising, storing an RNA-free mixture of the invention as described above or elsewhere herein at 5° C. or less for at least three days.

In some embodiments, the storing comprises storing the mixture for at least 14 day.

In some embodiments, the storing occurs at about 4° C.

In some embodiments, the mixture is frozen during the storing.

In some embodiments, the storing occurs at about –20° C. In some embodiments, the storing occurs at about –80° C.

In some embodiments, following the storing, further comprising contacting the reaction mixture with a sample comprising RNA under conditions to allow the reverse transcriptase to reverse transcribe the RNA, thereby producing a first-strand cDNA.

DETAILED DESCRIPTION OF THE INVENTION

I. Introduction

Figure 1:
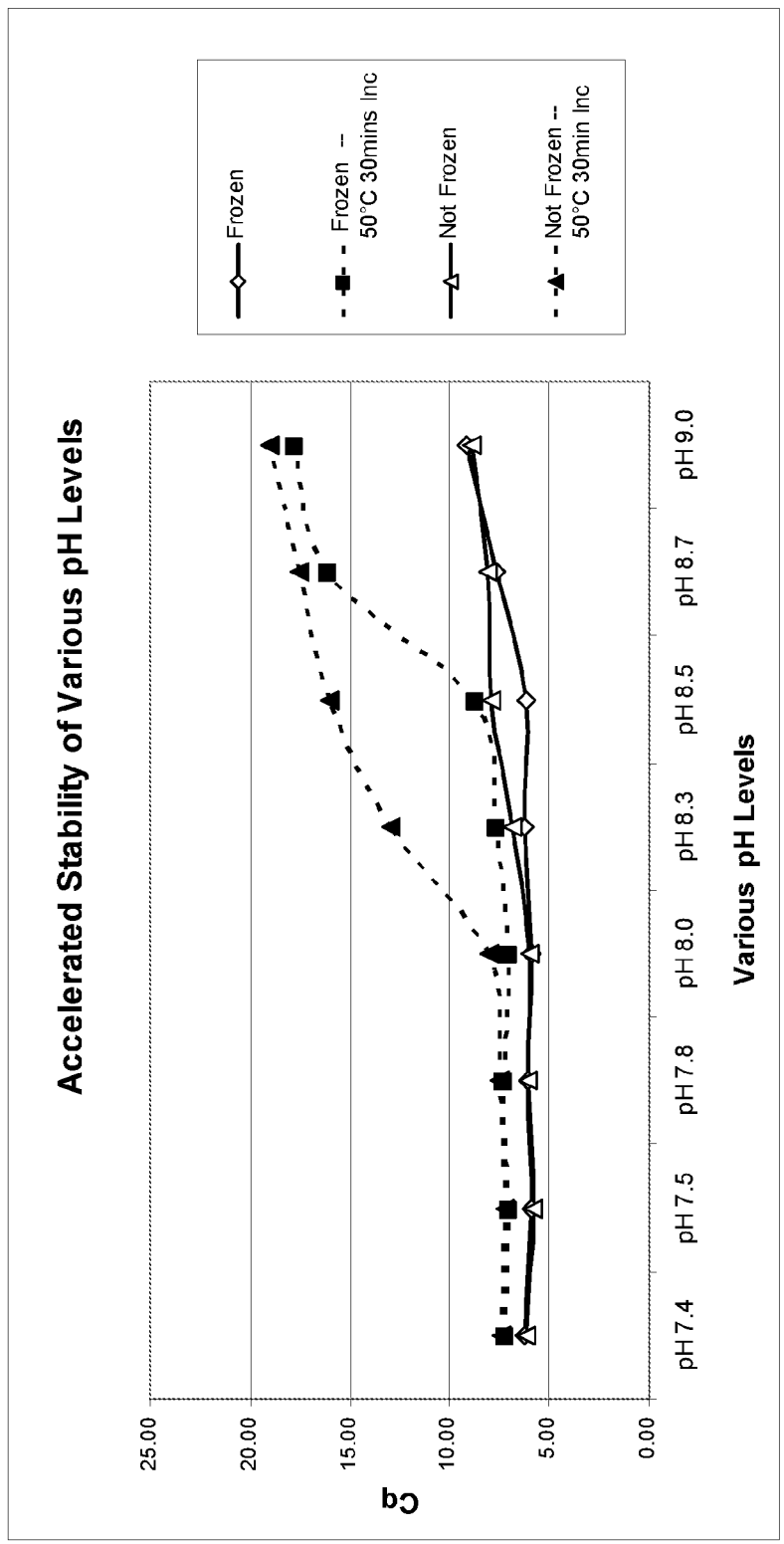
FIG. 1 illustrates accelerated stability results from reaction mixtures frozen and then pre-incubated at 50° C. for 30 minutes prior to RT-qPCR analysis. Control samples were not pre-incubated.

A reverse transcription (RT) reaction mixture formulation has been discovered that can be used in a "ready-to-use" format (i.e., containing reagents sufficient for an RT reaction except the template RNA), has improved storage stability, and allows for increased temperature of the RT reaction if desired.

Improved storage of the reaction mixtures described herein can be manifested, for example, in the ability of the mixtures to be frozen, thawed and then used in an RT reaction with essentially no change in the quantity of cDNA generated. Improved storage stability has been achieved in part by reduction of the pH of the reaction mixture from the standard pH~8.3 to a pH below 8 (e.g., pH 6-8). Many reverse transcriptase enzymes commonly used for generation of cDNA have an optimal pH (i.e., the pH at which activity is optimal) higher than 8. Therefore, historically reverse transcriptase enzymes have been used and stored at a pH higher than 8.

It has been further discovered that the inclusion of a buffer that exhibits minimal change in buffer capacity over changing temperature within the relevant temperature range for RT reactions and storage (e.g., in liquid samples between –20 and 50° C.) allows for improved stability of the reverse transcriptase, especially when transitioning between storage at colder temperatures (e.g., less than 4° C.) and use at warmer temperatures (e.g., 37° C. and higher).

Stability can be further increased by the inclusion of a relatively high concentration (at least 15%) of a polyol in the reaction mixture. While it is believed other polyols (for example, alcohols having four or more or five or more carbons) may also be effective, it has been found that the use of sorbitol (a six carbon alcohol), xylitol (a five carbon alcohol), or a combination thereof, further improves the thermal stability of reverse transcriptase in a reaction mixture.

As noted above, one benefit from the improved stability of the reaction mixtures of the invention is an improved ability to store reverse transcriptase mixtures while retaining enzyme activity. Yet another advantage is the improved thermostability of the enzymes, especially of enzymes whose activity is significantly harmed when held at temperatures greater than 42° C. at pH 8.3. It is believed that when a reaction mixture of the invention is combined with template RNA, one can perform RT reactions at higher temperature than would be possible with a standard RT reaction mixture. Elevated RT reaction temperatures can be useful, for example, in reducing the occurrence of RNA secondary structures than can interfere with the RT reaction.

II. Reaction Mixtures

Stabilized aqueous reaction mixtures comprising reverse transcriptase are provided. "Stable" enzyme reaction mixtures are reaction mixtures that, for example, can be stored at temperature below −20° C. for prolonged periods of time (e.g., at least 365, 550, or 730 days). "Stability" can also be demonstrated by performing an accelerated stability test involving stressing the mixture at 50° C. prior to testing its activity and then comparing the activity of the stressed mixture to a mixture that was not stressed. The reaction mixtures of the invention have improved stability, for example, compared to, standard commercial mixtures having a pH greater than 8 and containing Tris buffer.

The reaction mixtures described herein can comprise components sufficient for an RT reaction aside from the RNA template (i.e., as a "ready-to-use" formulation). This allows for reduced numbers of steps and solution transfers by a user thereby reducing the opportunity to introduce error or inconsistency into one's work. Accordingly, when prepared for commercial sale, the reaction mixtures will typically be sterile, for example, to avoid growth of microorganisms during storage and/or introduction of contamination into the RT reaction.

Any of a variety of reverse transcriptases can be used in the reaction mixtures of the invention. Exemplary reverse transcriptases include but are not limited to murine leukemia virus (MLV) reverse transcriptase, Avian Myeloblastosis Virus (AMV) reverse transcriptase, Respiratory Syncytial Virus (RSV) reverse transcriptase, Equine Infectious Anemia Virus (EIAV) reverse transcriptase, Rous-associated Virus-2 (RAV2) reverse transcriptase, SUPERSCRIPT II reverse transcriptase, SUPERSCRIPT I reverse transcriptase, THERMOSCRIPT reverse transcriptase and MMLV RNase H⁻ reverse transcriptases. The concentration of the reverse transcriptase can vary and optimal concentrations can be determined empirically and depend on the particular reverse transcriptase used. In some embodiments, the reverse transcriptase is at a concentration of between 10-50 units per microliter. It will be appreciated that the concentration of reverse transcriptase may differ depending on whether the reaction mixture is a "pre-mix" lacking the RNA template or the reaction mixture contains the additional volume of RNA template. In some embodiments, the reverse transcriptase will have an optimal pH activity above pH 8. In some embodiments, the reverse transcriptase is unstable (loses significant activity, for example, resulting in more than 1 Ct or Cq delay in an RT-qPCR of a target RNA) following incubation at pH 8.3 for 30 minutes at 50° C.

In some embodiments, the reaction mixtures have a pH of 8 or less, e.g., from 6 to 8, e.g. 6-7, 7-8, 6-7.5, 6.5-8, 7.5-7.7, 7.4-7.8, 7.6, etc.). In some embodiments, the reaction mixture having a pH within one of these ranges lacks template RNA but is otherwise "ready-to-use," i.e., such that RT occurs upon addition of template RNA and incubation at the appropriate temperature for the RT enzyme to function.

Alternatively, the reaction mixture can comprise template RNA, for example during an RT reaction. Generally, the pH of the reaction mixture will be maintained in part by the presence of a buffer. While it is believed any buffer compatible with RT reactions can be used, it can be further beneficial to use a buffer that does not significantly change buffering activity as a function of temperature with the range of storage and RT reactions (e.g., when in liquid phase between −20° and 50° C.). This can be advantageous, for example, when the reaction mixture is stored at relatively cold temperatures (e.g., 4°, −20°, or −80° C.) prior to use, e.g., at between 37°-50° C. In some embodiments, the buffer (when measured at a concentration of 0.1 M) has a change of no more than 0.01, 0.02, 0.025, 0.027, or 0.03 pH units per degree C. when between 20° and 37° C. This can be determined, for example, by measuring the pKa of the buffer at 20° and 37° C. and determining the difference in the pKa values divided by the number of degrees difference (17 degrees). Exemplary buffers that have a change of no more than 0.027 pH units per degree C. include, but are not limited to, HEPES ((4-(2-hydroxyethyl)-1-piperazineethanesulfonic acid)), ACES (N-(2-Acetamido)-2-aminoethanesulfonic acid), PIPES (piperazine-N,N'-bis(2-ethanesulfonic acid), MOPSO (3-(N-Morpholino)-2-hydroxypropanesulfonic Acid), BES (N,N-Bis(2-hydroxyethyl)-2-aminoethanesulfonic Acid), MOPS (3-(N-morpholino)propanesulfonic acid), TES (N-Tris(hydroxymethyl)methyl-2-aminoethanesulfonic acid), TAPSO (3-[N-Tris(hydroxymethyl)methylamino]-2-hydroxypropanesulfonic Acid), POPSO (Piperazine-N,N'-bis(2-hydroxypropanesulfonic acid)), BICINE (N,N-bis(2-hydroxyethyl)glycine), TAPS (N-Tris(hydroxymethyl) methyl-3-aminopropanesulfonic acid), and AMPSO (N-(1, 1-Dimethyl-2-hydroxyethyl)-3-amino-2-hydroxypropanesulfonic acid). Buffers can be used at concentrations appropriate for RT reactions when the reaction mixture is mixed with RNA template. In some embodiments, the buffer concentration ranges from 100 to 500 mM, e.g., about 250 mM.

Figure 2:
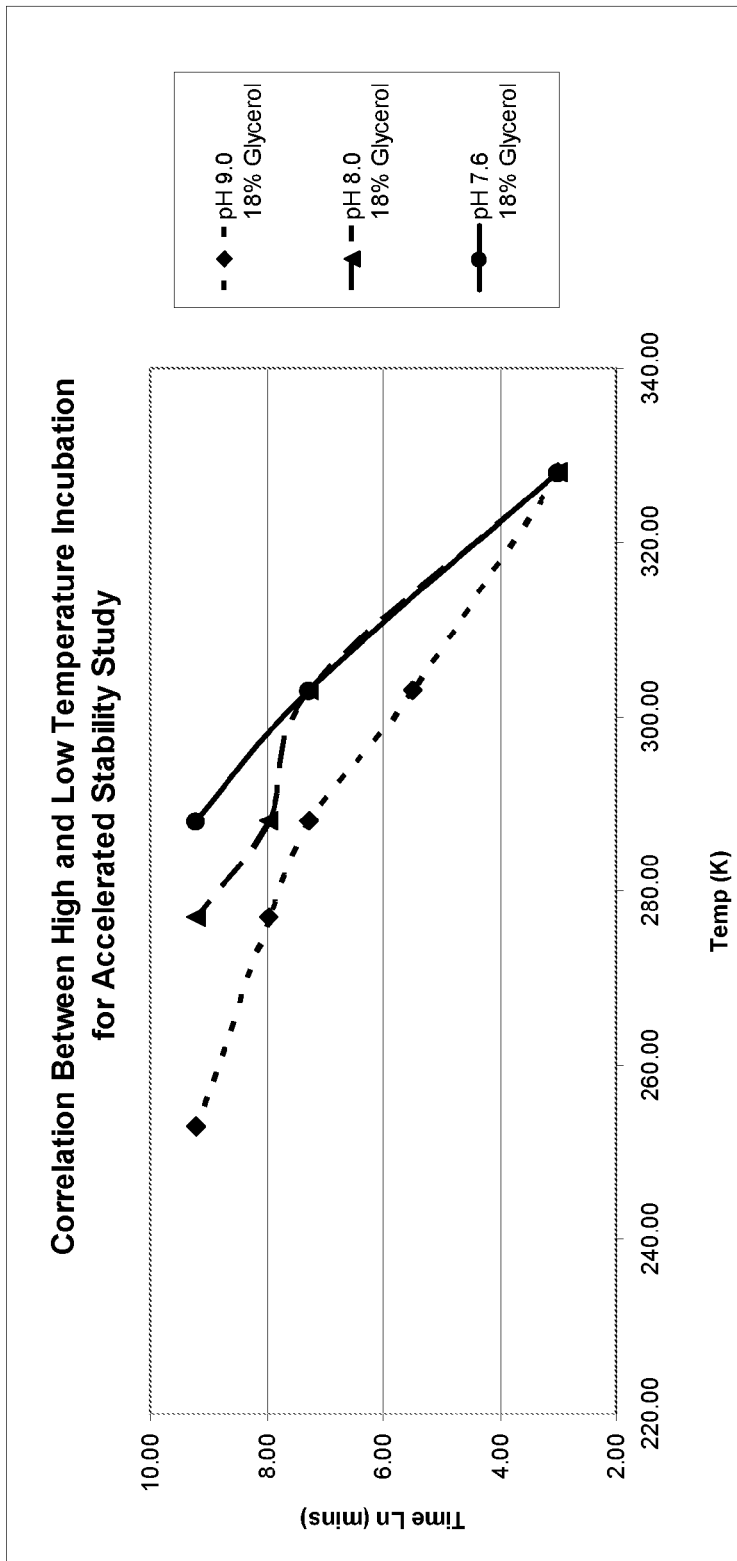
FIG. 2 illustrates the correlation of high and low temperature incubations in accelerated stability tests. The y-axis represents a stability time measurement in minutes indicating the time at which the reaction mixtures lose performance in RT-qPCR. The measurement is based on 1 Cq delay from its initial measuring point. If the mix is more stable, then more time has passes before the mixtures lose RT-qPCR performance. For example, at 288° K, mixtures having pH 7.6, 8.0 and 9.0 maintained real time stability of 10080, 2880, and 1440 minutes, respectively, demonstrating lower pH mixtures were more stable. Because the graph is linear for each of the mixes, the results show a correlation in accelerated stability, where the mixes are incubated at high temperature, compared to the real time stability, when the mixes are stored at low temperature such as 4° C. or –20° C.

In some embodiments, the reaction mixture comprises one or more polyol. In some embodiments, the polyol is a four or more carbon alcohol or a five or more carbon alcohol. In some embodiments, the total polyol concentration (i.e., the sum of the concentration of each polyol in the reaction mixture) is at least 10%, 15%, 20%, 25%, 30%, 35%, 40% or more. A variety of different polyols can be used. In some embodiments, the polyol is selected from sorbitol, xylitol, or a 4 carbon alcohol, a five carbon alcohol, a six carbon alcohol or is a combination thereof. As shown in FIG. 2, concentrations of at least 25% of sorbitol or xylitol are able to stabilize reverse transcriptase (stressed by heat at 55 C for 70 minutes), resulting in less than 1 Cq delay as measured by RT-qPCR when compared to an control sample that was not submitted to the stress heating step. Notably, concentrations of 35% or more polyol apparently completely stabilize the reverse transcriptase.

The reaction mixture can contain any additional component sufficient for, or that improves, an RT reaction. Exemplary additional components can include, but are not limited to, potassium chloride (e.g., 100-500 mM, e.g., about 250 mM), magnesium (e.g., as $MgSO_4$, e.g., 10-50 mM, e.g., about 25 mM), deoxytriphosphate nucleotides (e.g., dATP, dCTP, dGTP, dTTP, or analogs thereof), one or more detergents (e.g., Tween20, Triton X-100, NP40, etc., e.g., at 0.1-0.1%, e.g., about 0.05%), an oligo dT (e.g., dT12, dT20, or combinations thereof), an oligonucleotide other than an oligo dT (e.g., a mix of random sequences of a specified length (e.g., a hexamer) or one or more oligonucleotides specific for an RNA sequence of interest), an RNase inhibitor (e.g., Rnasin, RNaseA, etc.), or a combination thereof. In some embodiments, the reaction mixtures comprise a reducing agent. In some embodiments, the reaction mixtures do not comprise a reducing agent or at least does not comprise a sufficient amount of a reducing agent to significantly affect stability of the reverse transcriptase.

Generally, ready-to-use mixtures will contain most or all of the above-described ingredients. For example, in some embodiments, the reaction mixtures comprise, consist of, or consist essentially of, a reverse transcriptase (e.g., having a optimal pH above 8); a buffer (for example, HEPES, ACES, PIPES, MOPSO, BES, MOPS, TES, TAPSO, POPSO, BICINE, TAPS, or AMPSO); potassium chloride; magnesium; deoxytriphosphate nucleotides; one or more detergents; an oligo dT; an oligonucleotide other than an oligo dT; and optionally an RNase inhibitor and/or a di-cation chelator (e.g., EDTA). In some embodiments, the reaction mixtures comprise a reducing agent. In some embodiments, the reaction mixtures do not comprise a reducing agent or at least does not comprise a sufficient amount of a reducing agent to significantly affect stability of the reverse transcriptase.

The reaction mixtures can be packaged as part of a kit if desired, optionally with written instruction materials. Instruction materials can be in paper or electronic form, for example. In some embodiments, the kit can further comprise control samples (e.g., negative and/or positive controls). In some embodiments, the kit comprises a DNA polymerase, e.g., a thermostable polymerase capable of performing a PCR reaction in a thermocycler.

III. Reverse Transcription Reactions

Reverse transcription (RT) is an amplification method that copies RNA into DNA. RT reactions can be performed with reaction mixtures as described herein. For example, the invention provides for reverse transcribing one or more RNA (including for example, all RNA in a cell, e.g., to make a cDNA library) under conditions to allow for reverse transcription and generation of a first and optionally second strand cDNA. The RT reaction can be primed with a random primer, an oligo dT, or an RNA-specific primer. Components and conditions for RT reactions are generally known.

If desired, the reactions can further comprise RT-PCR. Standard techniques for performing PCR assays are known in the art (PCR Technology: Principles and Applications for DNA Amplification (Erlich, ed., 1989); PCR Protocols: A Guide to Methods and Applications (Innis, Gelfland, Sninsky, &, White, eds., 1990); Mattila et al., Nucleic Acids Res. 19: 4967 (1991); Eckert & Kunkel, PCR Methods and Applications 1: 17 (1991); Wallace et al., Ligase Chain Reaction, in Technologies for Detection of DNA Damage and Mutations, pp. 307-322 (Pfiefer, ed., 1996)). RT and PCR reactions are often used in the same assay and are referred to as RT-PCR. RT-PCR combines reverse transcription of RNA into DNA and subsequent DNA amplification reactions in a single reaction. Optimal reverse transcription, hybridization, and amplification conditions will vary depending upon the sequence composition and length(s) of the primers and target(s) employed, and the experimental method selected by the practitioner. Various guidelines may be used to select appropriate primer sequences and hybridization conditions (see, e.g., Sambrook et al., Molecular Cloning: A Laboratory Manual (2nd ed.) (1989); Ausubel, F. M. et al., eds. (1999) Short Protocols in Molecular Biology, 4th edition, John Wiley & Sons); Ausubel, F. M. et al., eds. (1999-2010) Current Protocols in Molecular Biology, John Wiley & Sons).

The practice of the present invention can employ conventional methods of chemistry, biochemistry, molecular biology, cell biology, genetics, immunology and pharmacology, within the skill of the art. Such techniques are explained fully in the literature. See, e.g., Gennaro, A. R., ed. (1990) Remington's Pharmaceutical Sciences, 18th ed., Mack Publishing Co.; Hardman, J. G., Limbird, L. E., and Gilman, A. G., eds. (2001) The Pharmacological Basis of Therapeutics, 10th ed., McGraw-Hill Co.; Colowick, S. et al., eds., Methods In Enzymology, Academic Press, Inc.; Weir, D. M., and Blackwell, C. C., eds. (1986) Handbook of Experimental Immunology, Vols. I-IV, Blackwell Scientific Publications; Maniatis, T. et al., eds. (1989) Molecular Cloning: A Laboratory Manual, 2nd edition, Vols. I-III, Cold Spring Harbor Laboratory Press; Ausubel, F. M. et al., eds. (1999-2010) Current Protocols in Molecular Biology, John Wiley & Sons; Ream et al., eds. (1998) Molecular Biology Techniques: An Intensive Laboratory Course, Academic Press; Newton, C. R., and Graham, A., eds. (1997) PCR (Introduction to Biotechniques Series), 2nd ed., Springer Verlag; Sambrook et al., Molecular Cloning: A Laboratory Manual (2nd ed.) (1989).

An advantage of the reaction mixtures of the invention is that the reaction mixtures allow for use of a reverse transcriptase in an RT reaction at a higher temperature than would otherwise be possible. Thus, for example, in embodiments in which 37° or 42° C. would be optimal for a particular reverse transcriptase, the reaction mixtures of the invention, and in particular reaction mixtures having a pH below 8, allow for the reverse transcriptase to perform an RT reaction above its optimal (e.g., 37° or 42° C.) temperature. Thus, in some embodiments, a non-thermostable reverse transcriptase is stored in a ready-to-use reaction mixture of the invention and then used to reverse transcribe one or more RNA at a temperature greater than 42° C., for example, between 43°-55°, 45°-550, 45°-50° C., etc. Higher temperature RT reactions are particularly helpful in situations where the template RNA forms secondary structure at normal RT temperatures (e.g., 37° or 42° C.) that partially or completely inhibit reverse transcription.

IV. Storage

Figure 4:
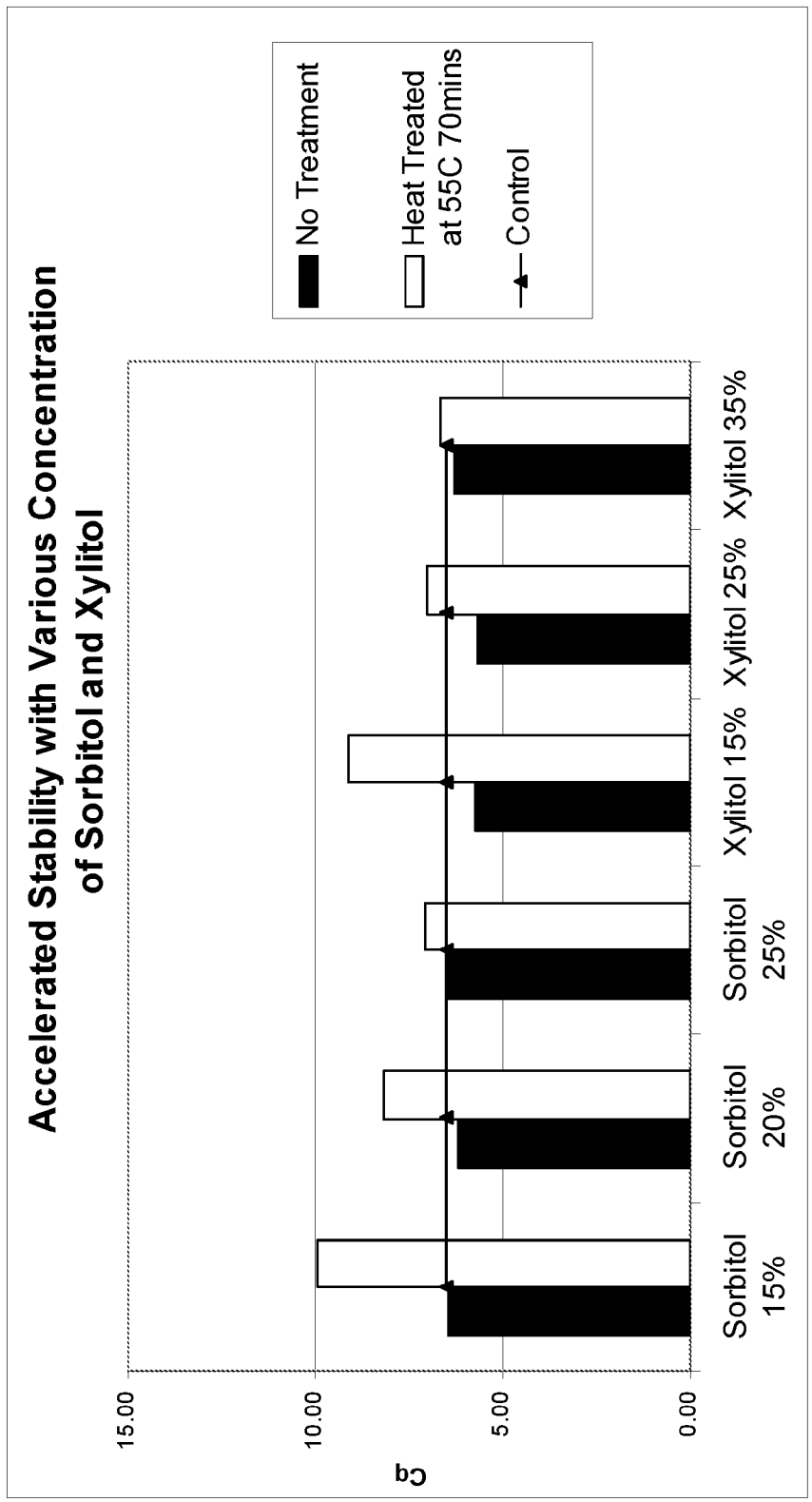
FIG. 4 illustrates results of accelerated stability tests of reaction mixtures containing various concentrations of xylitol or sorbitol.
Figure 5:
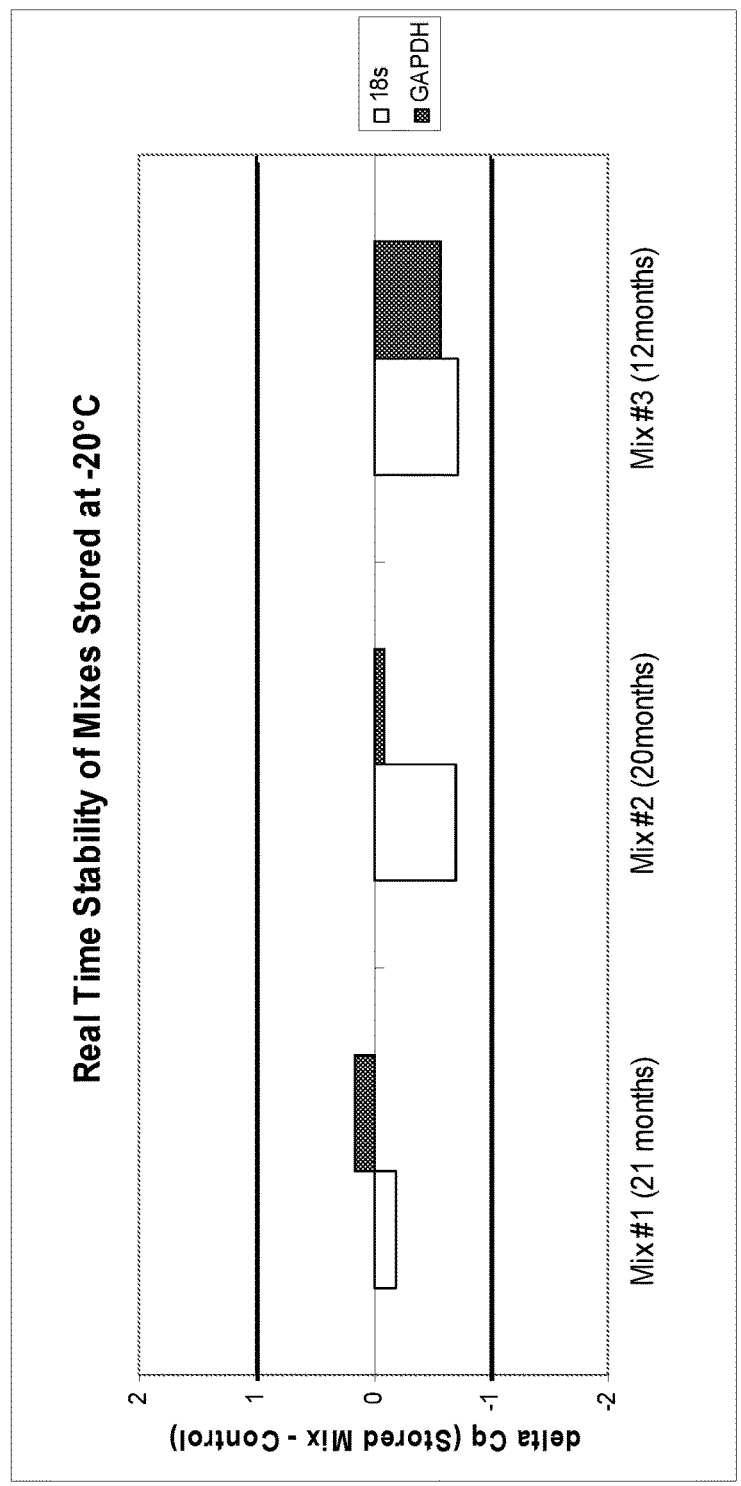
FIG. 5 illustrates real-time stability of mixes up to 21 months.

One advantage of the reaction mixtures of the invention is that they retain essentially all of their activity following storage at low temperatures (such as at 4 or −20° C.) or as demonstrated by accelerated stability tests, i.e., when the mixture are submitted to relatively high temperature (e.g., 50° or 55° C.) for a period of time. As shown in FIG. 1, illustrate a pattern: mixtures having a pH more than 8 were not as stable as mixtures having a pH less than 8 after storage for 2 days regardless of whether the mixtures were preheated or not. However the preheated samples show the pattern more clearly. Reaction mixtures having a pH of 8 and below did not significantly lose activity following the heat treatment. Similarly, FIG. 4 illustrates the improved stability of reverse transcriptase reaction mixtures containing various concentrations of polyols and demonstrates that increasing concentrations of these polyols stabilize the reverse transcriptase in accelerated stability tests.

Reaction mixtures of the invention, including but not limited to ready-to-use formulations, can be stored in aqueous form, e.g., frozen or liquid. In some embodiments, the reaction mixtures are stored for at least 1, 2, 5, 10, 20, 30 days or more without significantly losing reverse transcriptase activity. Reaction mixtures can be stored in liquid or frozen state depending on temperature and composition of the mixture, with higher concentrations of polyol (e.g. alcohols with four or more, or five or more, carbons) for example, allowing for the reaction mixture to remain in liquid form below 0° C., e.g., in some embodiments remaining liquid at around −20° C. In some embodiments, the reaction mixtures are stored at about 4 C, −20 C, or −80 C.

EXAMPLES

Example 1: Lower pH Improves Stability

Reaction mixtures comprising MLV reverse transcriptase and having various pH levels were stored frozen and in liquid state at −20 C by treating or not treating the mixes with a quick freeze on dry ice prior to storage. The reaction mixtures consisted of 250 mM Tris at pH 7.4, 7.5, 7.8, 8.0, 8.3, 8.7, and 9.0, 25 mM $Mg_2SO_4$, 250 mM KCl, 2.5 mM dNTPs, 5 µl of RTase, 1 mM EDTA, 28.4 µM of Oligo Primers and 12.5% Glycerol. After two days of storage at −20 C, sets of the mixtures, frozen or not frozen, were pre-incubated at 50° C. for 30 minutes prior to usage in RT-qPCR with 100 ng/rxn of Hela RNA to detect 18s RNA. Control samples were treated identically but were not pre-incubated at 50° C. The thermocycling condition for the RT step was 25° C. 5 mins, 42° C. 30 mins and 85° C. 5 mins and for the qPCR step was 95° C. 5 mins, 95° C. 10 sec 60° C. 30 sec×45 cycles plus a melt curve analysis.

The results of the experiment showed that both freezing and lowering the pH to 8 or below has an additive effect on storage stability. Moreover, lowering the pH significantly improves stability of both frozen and unfrozen mixtures. See, FIG. 1. Stressing the mixtures at an elevated temperature for a period of time prior to RT-qPCR resulted in a loss in performance when pH was increased from 8.0 to 8.5 between mixes that were frozen or liquid. Similarly, there was a loss of RT-qPCR activity when pH was raised to 9.0 with the frozen mixtures. By lowering the pH below 8.0, the storage stability of the mixtures were stabilized in the frozen or liquid mixtures regardless of whether the samples were pre-incubated at 50° C.

Example 2: Pre-Incubation at High Temperature Correlates to Low Temperature Storage Stability To illustrate that the accelerated stability test involving pre-incubation at 50° C. correlated to low temperature stability, several mixtures where incubated at various time points at various temperatures. Three different mixtures were stored at −20 C with the following compositions: 250 mM Tris at pH 9.0, 8.0 or 7.6, 25 mM $Mg_2SO_4$, 250 mM KCl, 2.5 mM dNTPs, 5 µl of RTase, 1 mM EDTA, 28.4 µM of Oligo Primers and 18% Glycerol. The mixtures were incubated at various time points and various temperatures prior to RT-qPCR with 100 ng/rxn of Hela RNA to detect 18s RNA. The thermocycling condition for the RT step was 25° C. 5 mins, 42° C. 30 mins and 85° C. 5 mins and the qPCR step was 95° C. 5 mins, 95° C. 10 sec 60° C. 30 sec×45 cycles plus a melt curve analysis.

FIG. 2 shows a correlation graph comparing the stability of the mixes incubated at high temperature and low temperature of time. As the incubation temperature increased, less time was needed to stress the mix before RT-qPCR performance was affected. Lowering the pH level of the mixture improved stability. For example, the slope of the mix at pH 7.6 was steeper compared to the others, demonstrating stability for longer periods of time at a given temperature. Based on an Arrhenius equation, the results provide an estimated shelf life of 4 years for the pH 7.6 sample when stored at −20° C.

Example 3: HEPES Buffer Provides Better Stability

Figure 3:
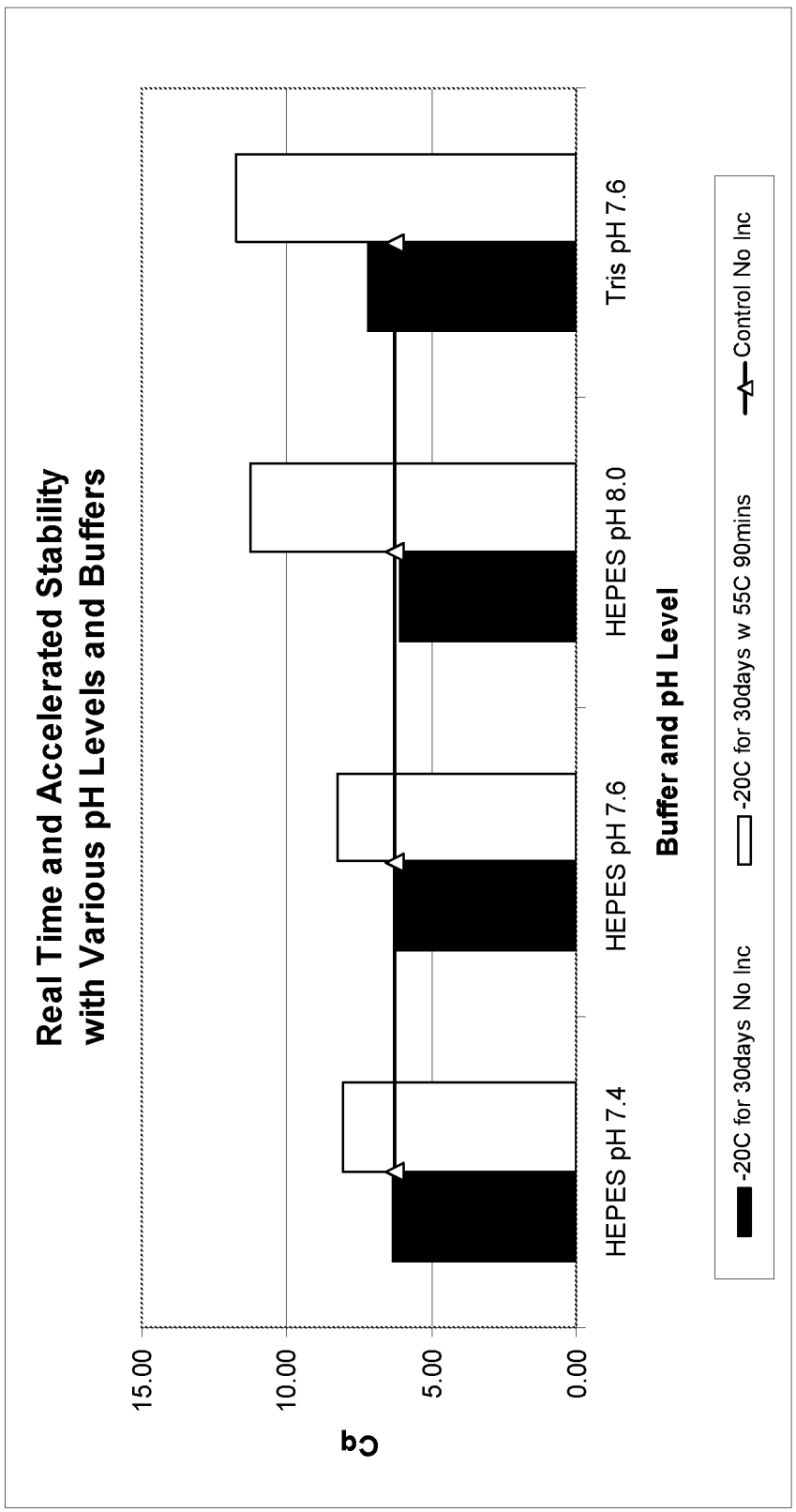
FIG. 3 illustrates results of RT qPCR for reaction mixtures having HEPES at different pH levels as well as a comparison to a mixture having Tris buffer.

It was also discovered that replacing Tris buffer with HEPES also improved the storage stability of the mixture. For example, HEPES-containing mixtures had improved stability based on incubations of 30 days at −20 C and also based on accelerated stability tests. The formulation tested consisted of 250 mM Tris pH 7.6 or 250 mM HEPES pH 7.4, 7.6 or 8.0, 25 mM $Mg_2SO_4$, 250 mM KCl, 2.5 mM dNTPs, 5 µl of RTase, 1 mM EDTA, 28.4 µM of Oligo Primers and 32% Glycerol. After 30 days of storage at −20° C., mixtures were pre-incubated at 55° C. for 90 minutes prior to usage in RT-qPCR with 100 ng/rxn of Hela RNA with 18s assay. Control mixtures were tested but were not pre-incubated at 55° C. The thermocycling condition for the RT step was 25° C. 5 mins, 42° C. 30 mins and 85° C. 5 mins and for the qPCR step was 95° C. 5 mins, 95° C. 10 sec 60° C. 30 sec×45 cycles plus a melt curve analysis. The control in FIG. 3 represents a freshly made mix prior to RT-qPCR with no pre-incubation step.

These data demonstrate that lowering the pH improves stability of the mixes in accelerated stability tests. In addition, based on the accelerated stability after 30 days, the HEPES pH 7.6 compared to the Tris pH showed better accelerated stability. By switching to HEPES, the small change in pH in respect to temperature helped stabilize the mix stored at −20 C.

Example 4: Increasing in Sorbitol and Xylitol Concentration Improves Stability

FIG. 4 shows data from experiments in which the mixtures have increasing amounts of sorbitol and xylitol. Mixtures were treated with or (control) without a pre-incubation step for 55° C. for 70 minutes prior to RT-qPCR. Each mixture consisted of 250 mM HEPES pH 7.6, 25 mM $Mg_2SO_4$, 250 mM KCl, 2.5 mM dNTPs, 5 µl of RTase, 1 mM ETDA, 40 µM Oligo Primers, and 15%-35% xylitol or 15%-25% sorbitol. The mixtures were treated with or without the pre-incubation step, followed by RT-qPCR with 18s primer set, 100 ng/rxn of Hela RNA and iQ SBYR SuperMix (Bio-Rad, Hercules, Calif.). The thermocycling condition for the RT step was 25° C. 5 mins, 42° C. 30 mins and 85° C. 5 mins and for the qPCR step was 95° C. 5 mins, 95° C. 10 sec 60° C. 30 sec×45 cycles plus a melt curve analysis. The control ("no treatment") represents a freshly made mix prior to RT-qPCR with no pre-incubation step.

Lowering the pH and increasing the sugar (polyol) of a reaction mixture improves the stability of reaction mixtures. The data demonstrates that increasing the amount of sorbitol or xylitol from 15% to 35% helps stabilize the mixtures. As sorbitol or xylitol concentration is increased, there is less change in RT-qPCR performance between the treated (pre-incubated) or untreated samples at elevated temperature. Based on the accelerated stability studies, an estimate shelf life of 4 years can be expected from mixtures having 25% sorbitol or 35% xylitol.

Example 5: Mixes Shows Real Time Stability for Up to 21 Months

Several mixes, which are identical in composition, were stored at −20° C. for 21, 20 and 12 months and measured functionally by RT-qPCR to determine the relative stability to a control mix. The comparison of each mix shows less than 1 ΔCq difference to the control mix. Each mixture consist of 250 mM HEPES pH 7.6, 25 mM $Mg_2SO_4$, 250 mM KCl, 2.5 mM dNTPs, 5 μl of RTase, 1 mM ETDA, 40 μM Oligo Primers, and Polyol. The mixes were used to synthesize cDNA from 100 ng/rxn of Hela RNA with 18s and GAPDH primer sets and followed by qPCR with iQ SBYR SuperMix (Bio-Rad, Hercules, Calif.). The thermocycling condition for the RT step was 25° C. 5 mins, 42° C. 30 mins and 85° C. 5 mins and for the qPCR step was 95° C. 5 mins, 95° C. 10 sec 60° C. 30 sec×45 cycles plus a melt curve analysis. The control represents a freshly made mix in RT-qPCR.

The examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A sterile aqueous reaction mixture comprising sufficient ingredients, except template RNA, for reverse transcription of RNA, the mixture comprising:
   a reverse transcriptase having an optimal pH above 8;
   deoxytriphosphate nucleotides; and
   a buffer, wherein the buffer is selected from the group consisting of Tris, HEPES, ACES, PIPES, MOPSO, BES, MOPS, TES, TAPSO, POPSO, BICINE, TAPS, and AMPSO,
   wherein said sterile aqueous reaction mixture has a pH of between 6-8
   and lacks template RNA.

2. The sterile aqueous reaction mixture of claim 1, wherein said buffer, when measured at a concentration of 0.1 M, has a change of no more than 0.027 pH units per degree Celsius when between 20° C. and 37° C.

3. The sterile aqueous reaction mixture of claim 1, further comprising one or more polyols having a total polyol concentration of at least 15%, wherein said polyol is a four or more carbon alcohol.

4. The sterile aqueous reaction mixture of claim 3, wherein said polyol is selected from the group consisting of sorbitol and xylitol.

5. The sterile aqueous reaction mixture of claim 1, wherein said reverse transcriptase is selected from the group consisting of murine leukemia virus (ML V) reverse transcriptase, Avian Myeloblastosis Virus (AMV) reverse transcriptase, Respiratory Syncytial Virus (RSV) reverse transcriptase, Equine Infectious Anemia Virus (EIAV) reverse transcriptase, Rous-associated Virus-2 (RAV2) reverse transcriptase, SUPERSCRIPT II reverse transcriptase, SUPERSCRIPT I reverse transcriptase, THERMOSCRIPT reverse transcriptase and MMLV RNase H reverse transcriptase.

6. The sterile aqueous reaction mixture of claim 1, wherein said sterile aqueous reaction mixture further comprises potassium chloride, magnesium, one or more detergents, an oligo dT, an oligonucleotide other than an oligo dT, an RNase inhibitor, or a combination thereof.

7. The sterile aqueous reaction mixture of claim 1, consisting of said reverse transcriptase, said buffer, potassium chloride, $MgSO_4$, one or more polyol(s), EDTA, and oligonucleotides.

8. The sterile aqueous reaction mixture of claim 1, wherein said reverse transcriptase is selected from the group consisting of SUPERSCRIPT II reverse transcriptase, SUPERSCRIPT I reverse transcriptase, THERMOSCRIPT reverse transcriptase and MMLV RNase H-reverse transcriptase.

9. The sterile aqueous reaction mixture of claim 1, further comprising one or more detergents.

10. The sterile aqueous reaction mixture of claim 1, further comprising an oligo dT oligonucleotide.

11. The sterile aqueous reaction mixture of claim 1, wherein said buffer is at a concentration of between 100-500 mM.

12. A method of storing a sterile aqueous reaction mixture comprising storing the sterile aqueous reaction mixture of claim 1 at 5° C. or less for at least three days.

13. The method of claim 12, wherein said storing comprises storing said sterile aqueous reaction mixture for at least 14 days.

14. The method of claim 12, wherein said storing occurs at 4° C.

15. The method of claim 12, wherein said sterile aqueous reaction mixture is frozen during said storing.

16. The method of claim 12, wherein, following said storing, contacting said sterile aqueous reaction mixture with a sample comprising RNA under conditions to allow the reverse transcriptase to reverse transcribe said RNA, thereby producing a first-strand cDNA.

* * * * *